United States Patent [19]

Czarniecki et al.

[11] Patent Number: 4,857,301

[45] Date of Patent: Aug. 15, 1989

[54] SULFONAMIDE COMPOUNDS, COMPOSITIONS AND METHOD OF USE

[75] Inventors: Michael F. Czarniecki, Westfield; Barr E. Bauer, Elmwood Park, both of N.J.

[73] Assignee: Schering Corporation, Kenilworth, N.J.

[21] Appl. No.: 101,038

[22] Filed: Sep. 25, 1987

[51] Int. Cl.⁴ .................... A61K 31/47; C07D 401/12
[52] U.S. Cl. ........................................ 424/40; 424/408; 514/307; 514/309; 514/312; 514/314; 546/139; 546/141; 546/144; 546/145; 546/147; 546/153; 546/157; 546/172
[58] Field of Search ............... 546/139, 141, 145, 144, 546/147, 153, 157, 167, 172; 514/307, 309, 312, 314; 424/40, 408

[56] References Cited

U.S. PATENT DOCUMENTS

| | | | |
|---|---|---|---|
| 4,425,589 | 6/1985 | Hidaka et al. | 544/128 |
| 4,456,757 | 6/1984 | Hidaka et al. | 546/139 |
| 4,634,770 | 1/1987 | Hidaka et al. | 546/139 |
| 4,678,783 | 7/1987 | Hidaka et al. | 546/139 |

FOREIGN PATENT DOCUMENTS

| | | |
|---|---|---|
| 0061673 | 10/1982 | European Pat. Off. . |
| 0109023 | 5/1984 | European Pat. Off. . |
| 0187371 | 7/1986 | European Pat. Off. . |

OTHER PUBLICATIONS

Itzkowitz, "Chemical Abstracts", vol. 67, 1967, col. 6959z.

Atlas et al., "Chemical Abstracts", vol. 97, 1982, col. 97:85100h.

*Primary Examiner*—Richard L. Raymond
*Assistant Examiner*—James H. Turnipseed
*Attorney, Agent, or Firm*—Joseph T. Majka; James R. Nelson; Stephen I. Miller

[57] ABSTRACT

Certain substituted sulfonamide quinolines and isoquinolines are disclosed having anti-allergic activity. A preferred use is for the treatment of chronic obstructive lung disease, and in particular, asthma.

22 Claims, No Drawings

SULFONAMIDE COMPOUNDS, COMPOSITIONS AND METHOD OF USE

BACKGROUND OF THE INVENTION

The present invention relates to certain quinoline and isoquinoline sulfonamide compounds, pharmaceutical compositions containing said compounds and methods of using said compounds.

European Patent Application No. 851165020.9, published July 16, 1986, and U.S. Pat. No. 4,525,589 disclose related sulfonamides. Also European Patent Application No. 109,023 published on May 23, 1984 and European Patent Application No. 61,673 published on Oct. 6, 1982 similarly disclose related sulfonamides. None of the references discloses substituted sulfonamides for use as anti-allergic compounds.

SUMMARY OF THE INVENTION

This invention encompasses a compound represented by structural formula I

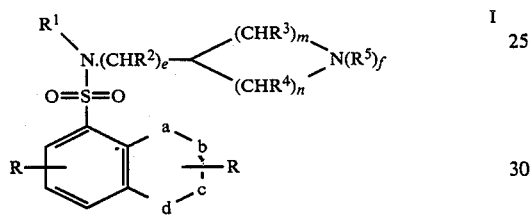

or a pharmaceutically acceptable salt or solvate thereof, wherein:

one of a, b, c and d is =N— and the remaining a, b, c and d groups are =CH—, one of which may be substituted with R;

each R optionally represents halo, lower alkyl, alkenyl, alkynyl, aryl, heteroaryl or hydroxy;

$R^1$ and $R^2$ independently represent H or lower alkyl;

e is an integer of from 0 to 5;

$R^3$ and $R^4$ independently represent H, lower alkyl, alkenyl, alkynyl, aryl or heteroaryl;

m and n are independently 0, 1, 2, 3 or 4 such that the sum of m and n is 3, 4, 5 or 6; and $R^5$ represents H, lower alkyl, —$CO_2R^a$, lower alkyl substituted with —$CO_2R^a$ (where $R^a$ is lower alkyl) or aminoiminomethyl such that when $R^5$ is H or lower alkyl, f is the integer 1 or 2, and when $R^5$ is aminoiminomethyl or $CO_2R^a$, f is 1.

A preferred group of compounds of the invention is represented by formula I wherein b or c represents =N—, most preferably c represents =N—, and a, b and d are CH.

A more preferred group of compounds of the invention is represented by formula I with c representing =N—, a, b and d are =CH— and $R^1$ and $R^2$ representing H. A still more preferred group of compounds of the invention is represented by formula I wherein c represents =N—, a, b, and d are =CH—, $R^1$ and $R^2$ are H and e is 0, 1 or 2.

The most preferred group of compounds of the invention is represented by formula I wherein c is =N—, a, b and c are =CH—, e is 1 or 2, m and n are 2 and $R^3$, $R^4$ and $R^5$ are H.

Preferred species falling within the scope of the invention include:

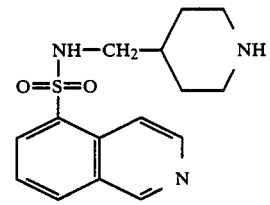

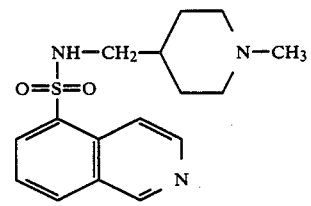

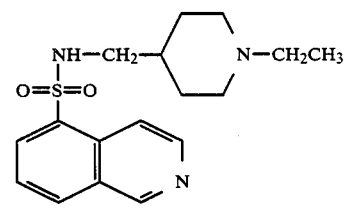

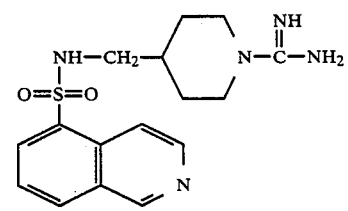

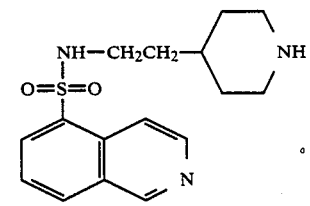

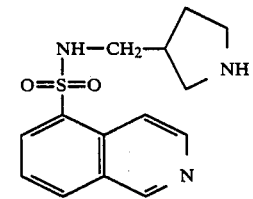

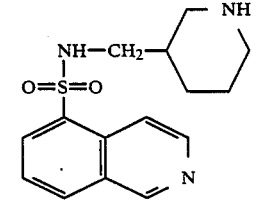

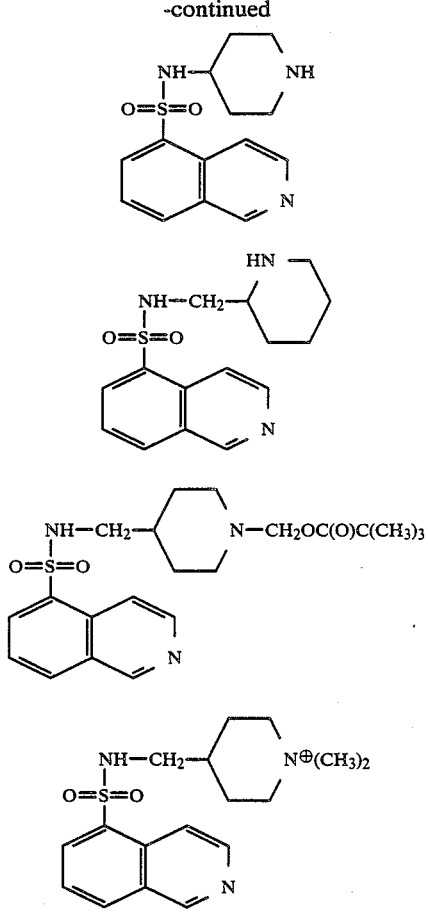

The invention includes a pharmaceutical composition comprising represented by formula I or a pharmaceutically acceptable salt or solvate thereof in combination with a pharmaceutically acceptable carrier.

The invention also includes a method of treating allergy comprising administering to a mammal in need of such treatment an anti-allergic effective amount of a compound represented by formula I or a pharmaceutically acceptable salt or solvate thereof.

As used herein, the following terms are used as defined below unless otherwise indicated:

alkyl—straight, branched or cyclic carbon chains containing from 1 to 20 carbon atoms;

lower alkyl—straight or branched carbon chain containing from 1 to 6 carbon atoms;

halo—chloro, bromo, fluoro or iodo;

alkenyl—straight or branched carbon chain containing from 2 to 20 carbon atoms and at least one carbon to carbon double bond;

alkynyl—straight or branched carbon chain containing from 2 to 20 carbon atoms and at least one carbon to carbon triple bond;

aryl—(including the aryl portion of heteroaryl) a carbocyclic group containing from 5 to 15 carbon atoms and having at least one aromatic ring (e.g. phenyl ring) with all available substitutable carbon or hetero (e.g. nitrogen) atoms of the group being a possible point of attachment.

heteroaryl—represents a carbocyclic group containing from 6 to 15 carbon atoms, said carbocyclic group being interrupted with from 1 to 3 hetero atoms, —O—, —S— or —N—, said carbocyclic group containing at least one aromatic ring, said heteroatoms being located in the aromatic ring;

pharmaceutically acceptable salt—compound prepared by reaction of an acid and base to form a pharmacologically suitable form of the compound, which possesses the appropriate solubility, bioequivalence and pharmacological activity, such as acid addition salts of inorganic acids, e.g., hydrochloric, hydrobromic, phosphoric and sulfuric acids. Also included are the salts of organic acids, such as acetic, citric, tartaric, lactic, succinic, fumaric, maleic, methanesulfonic and p-toluenesulfonic acids, as well as the quaternary ammonium compounds, where the N in the saturated heterocyclic ring is quaternized, with e.g., alkyl groups.

pharmaceutically acceptable solvate-molecular or ionic complex of molecules or ions of solvent with a compound of formula I.

DETAILED ESCRIPTION

Certain compounds of the invention may exist in isomeric forms. The invention includes all such isomers, both in pure forms and in admixture, including racemic mixtures.

Certain compounds of the invention can exist in solvated or unsolvated forms, including hydrated forms, e.g., hemihydrate. In general the solvated forms, with pharmaceutically acceptable solvents, such as water, ethanol and the like are equivalent to the unsolvated forms for purposes of the invention.

Certain basic compounds of the invention form pharmaceutically acceptable salts, such as for example, the piperidine nitrogen, which can be quaternized and form salts with strong acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form of the compound with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of the invention.

All acid and quaternary ammonium salts are intended to be pharmaceutically acceptable salts within the scope of the invention and all acid salts are considered equivalent to the free forms of the corresponding compounds for purposes of the invention.

The compounds of the invention contain an aromatic nitrogen in the fused ring system, indicated at one of positions a, b, c or d. The remaining a, b, c and d groups are CH which may be substituted with R.

To make a compound of formula I, a fused aromatic ring sulfonyl chloride is reacted with the appropriate primary or secondary amine in the presence of an organic base, one example of which is triethylamine. The fused aromatic ring sulfonyl chloride may be prepared from commercially available products, such as isoquinoline and chlorosulfonic acid.

Quinoline may be substituted into the reaction in place of isoquinoline to prepare compounds where the N of the fused ring system is located in position one.

Substituted quinolines and isoquinolines may be prepared by direct chlorosulfonation of the aromatic nucleus using chlorosulfonic acid. Substituted groups may be added to the quinoline or isoquinoline by conventional methods, such as is described in Acheson, *An Introduction to the Chemistry of Heterocyclic Compounds*, 3d ed, pp. 298 to 329, (1976) the teachings of which are incorporated herein by reference.

Alternatively an appropriately substituted aminoquinoline or aminoisoquinoline derivative may be treated with nitrous acid prepared from sodium nitrite and hydrochloric acid, then sulfur dioxide and cupric bromide to form the substituted quinoline or isoquinoline sulfonyl chloride.

Another alternative is to treat an appropriately substituted quinoline or isoquinoline aryl bromide with an alkyl lithium to form an intermediate aryl lithium compound, which may subsequently treated with sulfur dioxide to form a stable aryl sulfinate salt. The salt may be oxidized with sulfuryl chloride to yield the substituted aryl sulfonyl chloride.

The general reactions described in Preparative Examples 1 and 2 produce the 5- and 8-chlorosulfonyl isoquinolines as well as the 5- and 8-quinoline sulfonylchlorides. Throughout this specification, in addition to the 5-isoquinoline analogs which are exemplified, the 8-substituted isoquinoline and the 5- and 8-substituted quinoline analogs can be produced by simply substituting said alternative fused ring system in place of the 5-substituted isoquinoline. Consequently, the scope of the invention includes the 5- and 8-substituted isoquinoline derivatives as well as the 5- and 8-substituted quinoline derivatives.

When preparing compounds of the invention, it is frequently necessary to protect the groups in column one below of the following table. Conventional protecting groups are effective. Such groups in protected form appear in column two.

| 1. Group to be protected | 2. Protected Group |
| --- | --- |
| $\diagdown\!\!\!\diagup$NH | $\diagdown\!\!\!\diagup$NC(O)alkyl, $\diagdown\!\!\!\diagup$NC(O)benzyl, $\diagdown\!\!\!\diagup$NC(O)phenyl |
| —OH | 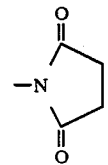 |
| —COOH | —CO$_2$alkyl, —CO$_2$benzyl, —CO$_2$phenyl |
| —NHR$^a$ where R$^a$ is a heterocycloalkyl or alkyl heterocycloalkyl group. | —NR$^a$—⟨O⟩, —NR$^a$C(O)CH$_3$, —NR$^a$CH$_2$—⟨phenyl⟩ |

| 1. Group to be protected | 2. Protected Group |
| --- | --- |
| —NH$_2$ | —N(succinimide) |

The sulfonyl chloride precursor compound may be condensed with the appropriate primary or secondary amine in the presence of an organic base, such as triethylamine, in an appropriate solvent. Purification can be effected as necessary, such as using normal phase silica chromatography, or reverse phase column chromatography.

To prepare a compound where R$^5$ in formula I is lower alkyl, the cycloalkylamine may be protected and subjected to reductive alkylation with an appropriate aldehyde and thereafter condensed with the appropriate aryl sulfonyl chloride.

To prepare compounds of the invention where R$^3$ and R$^4$ represent substituent groups, the appropriately substituted aromatic ring, such as pyridine, may be substituted and may then undergo catalytic reduction. The nitrogen containing ring, with the optional substituent groups attached may be condensed with the quinoline or isoquinolinesulfonyl chloride to yield a compound of the invention.

Salts such as quaternary ammonium compounds of the invention may be prepared by protecting the primary or secondary-amino side chain, alkylating the cyclic amino group, deprotecting the amino side chain and coupling with aryl sulfonyl chloride.

The compounds represented by formula I are useful for treating allergy in a mammal in need of such treatment. The preferred anti-allergic use is the treatment of chronic obstructive lung disease. As used herein, the term chronic obstructive lung disease means disease conditions in which the passage of air into and out of the lungs is obstructed or diminished, such as is the case in asthma, bronchitis and the like. The anti-allergic activity of the compounds of the invention is assessed using the test procedures described below.

Compounds

For in vitro experiments, the compounds tested are prepared as a stock solution in DMSO and diluted with physiological buffer into the final desired concentration. For studies when the compounds are given i.v., the compounds are dissolved in saline (0.9%). When given intraduodenally or orally, the compounds are suspended in a methylcellulose vehicle. For the intratracheal administration of drugs, the compounds are suspended or dissolved in 0.5% Tween 20 in saline.

In vivo, the compounds of the invention inhibit bronchoconstriction to different spasmogens e.g., histamine and methacholine, including an SRS-A mediated anaphylactic bronchoconstriction in guinea pigs.

The compounds of the invention are useful for reversing as well as inhibiting bronchoconstrictions. Hence, the compounds of the invention are useful for treating allergy symptomatically, i.e. to relieve symptoms which are present, or prophylactically. The compounds of the invention are particularly effective when administered directly to the tracheobronchial tree, such as by an inhalation aerosol.

MATERIALS AND METHODS

A. Antibronchoconstrictor Activity in Vitro

Male Hartley guinea pigs (300–400 g) were sacrificed by stunning, and the trachea removed and cut into 5 mm segments. The segments were suspended in 10 ml organ baths containing Krebs-Henseleit bicarbonate buffer (NaCl, 6.78; $CaCl_2$, 0.28; KCl, 0.042; $MgSO_4$, 0.29; $NaH_2PO_4$, 0.18; $NaHCO_3$, 2.1 and glucose 1.0 g/l). The buffer is maintained at 37° C. and oxygenated with 95% $O_2$ and 5% $CO_2$. The tissues are attached to force displacement transducers for the measurement of isometric tension. The tracheal segments are allowed to equilibrate for 60 minutes under a resting tension of 2 g.

1. Inhibition of Calcium-Induced Contractions

The compounds are evaluated for inhibition of calcium-induced contractions of isolated guinea pig trachea. The tracheas are exposed to 16 mM KCl in normal buffer for 10 minutes and washed in calcium-free buffer. The segments are then allowed to equilibrate for 40 minutes in calcium-free buffer and then rechallenged with 16 mM KCl. A cummulative concentration response curve to $CaCl_2$ may be generated in the presence or absence of a test compound which is added 20 min before the addition of $CaCl_2$. A percent inhibition of the response to $Ca^{2+}$ may be calculated for each compound. For example, the compound 5-(4-piperidinylmethyl)aminosulfonyl isoquinoline inhibits calcium induced contractions by 65 percent when administered at a 10 micromolar concentration using by the abovedescribed procedure

2. Bronchorelaxant Activity

The ability of compounds of the invention to relax respiratory smooth muscle may be demonstrated using basal toned guinea pig trachea in normal Krebs-Henseleit bicarbonate buffer. A cumulative concentration-response curve may be generated for the test compound using logarithmically spaced concentrations. Each concentration of test compound is allowed to act until the response reaches a stable plateau, and then the next higher concentration is added. For each concentration of compound the percent relaxation may be calculated.

For example, 5-(4-piperidinylmethyl) aminosulfonyl isoquinoline reduces the basal tone of isolated guinea pig trachea by 68 percent when administered at a 100 micromolar concentration, using procedure 2 above.

B. Antibronchoconstrictor Activity in Anesthetized Guinea Pigs

Activity of the compounds of the invention may also be demonstrated using male Hartley guinea pigs ranging in weight from 350 to 450 g. The animals are anesthetized with an intraperitoneal injection of 0.9 ml/kg dialurethane (containing 0.1 g/ml diallylbarbituric acid, 0.4 g/ml ethylurea and 0.4 g/ml urethane) and surgically prepared with catheterization of the trachea, jugular vein and in some animals, the carotid artery. The animals are mechanically ventilated with a Harvard rodent respirator to deliver a tidal volume of 4 ml at 60 breaths/min. A precalibrated pressure transducer (Statham, Model P23Id) is connected to a side-port in the tracheal cannula and the intratracheal pressure is measured using a pulmonary function computer system (Schering Corporation, N.J.). Using this system, drug responses may be tested for the ability to modify tracheal pressure using the technique of Konzett, Rossler, "Versuchsanordnunguntersuchungen an der Bronchialmuskulatur. Naunyn-Schmied" *Arch. Exp. Path. Pharmak.* 195: 71–77. (1940) with the modifications of Tozzi and Taylor *Fed. Proc.* 24: 204. (1965).

1. Inhibition of Bronchoconstriction

For this assay, histamine dihydrochloride (2–4 ug/kg) or methacholine chloride (2-4 ug/kg) is injected as an intravenous bolus to induce bronchospasm. Three or four separate injections of the spasmogen are performed in each animal. The bronchospasm induced by the first two injections is averaged to represent predrug responses. A single dose of a test compound or a placebo is then administered either intravenously (volume equivalent of 1 ml/kg) o intratracheally (a volume of 0.1 ml instilled through the tracheal cannula with a micropipette), followed by a separate injection of histamine or methacholine at a selected time interval after administration of the test compound. For each dose of compound a percent inhibition of pre-drug bronchoconstriction may be calculated.

For example, intravenous administration of 5-(4-piperidinylmethyl)aminosulfonyl isoquinoline as described above at a dose of 1 mg/kg inhibits histamine induced bronchospasm by 41 percent, and inhibits methacholine induced bronchospasm by 50 percent. Similarly, when 5-(4-piperidinylmethyl)aminosulfonyl isoquinoline is administered intravenously at a dose of 10 mg/kg, histamine induced bronchospasm is inhibited by 72 percent and methacholine induced bronchospasm is inhibited by 85 percent.

2. Bronchodilator Activity

Bronchodilator activity may be measured as the reversal of bronchoconstriction induced by the subcutaneous administration of a large (1 mg/kg) dose of histamine dihydrochloride. When the resulting bronchospasm had reached a stable plateau, the test compounds are administered i.v., (in a volume of 0.1 ml) and the decrease in intratracheal pressure is recorded. Reversal of the bronchoconstriction may be calculated as a percent of the maximum reversal in each animal produced with the administration of salbutamol sulfate (1 mg/kg i.v.) a known bronchodilator. When for example, 5-(4-piperidinylmethyl)aminosulfonyl isoquinoline is administered intravenously at a dose of 3 mg/kg, bronchospasm is inhibited by 27 percent. When the dosage of 5-(4-piperidinylmethyl)aminosulfonyl isoquinoline is increased to 10 mg/kg, bronchospasm is inhibited by 75 percent.

C. Antibronchoconstrictor Activity in Conscious Guinea Pigs

The guinea pigs are placed inside a whole body plethysmograph as described by Amdur and Meac, "Mechnaics of respiration in unanesthetized guinea pigs", *Am. J. Physiol* 192: 364–368. (1958). Pressure fluctuations within the plethysmograph are measured for computation of tidal volume using a pulmonary function computer (Buxco electronics, Sharon, Conn.). The tidal volume signal is displayed every minute on a printer. To augment the tidal volume signal, guinea pigs breathe a gas mixture enriched with $CO_2$ (10% $CO_2$, 21% $O_2$, 69% $N_2$) for the period of study.

Bronchoconstriction is measured as the peak reduction of tidal volume produced by histamine solution (0.05%) delivered as an aerosol generated from an ultrasonic nebuliser (deVilbiss, Model 65) for 30 seconds. Animals received either a test compound or vehicle placebo given orally one hour before histamine challenge. For example, the compound 5-(4-piperidinylmethyl)aminosulfonyl isoquinoline inhibits histamine induced bronchospasm by 21 percent when administered orally at a dose of 30 mg/kg.

When administered to a patient for the treatment of allergy, the compounds of the invention may be administered in an amount ranging from about 0.1 mg to about 1000 mg per day, said amount being effective for the treatment of allergy. The dosage may be administered in single or multiple daily doses, and may be administered to reduce the allergic symptoms or prophylactically to prevent their occurrance. The compound may be administered in the above described dosage range by any conventional route of administration, such as by administering a composition described herein.

For preparing pharmaceutical compositions from the compounds of this invention, inert, pharmaceutically acceptable carriers are typically used which can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired.

The powders or tablets may typically contain active ingredients ranging from about 5 to about 70 percent on a w/w basis. Suitable solid carriers include magnesium carbonate, magnesium stearate, talc, sugar, lactose, pectin, dextrin, starch, gelatin, tragacanth, methylcellulose, sodium carboxymethylcellulose, a low melting point wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting point wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations may include solutions, suspensions and emulsions. For example, water or water-propylene glycol solutions are useful for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Aerosol preparations suitable for inhalation may include solutions or solids in powder form, which may be in combination with a pharmaceutically acceptable carrier, such as an inert compressed gas. Inhalation aerosols may be packaged in a pressure resistant container, which may have a metered dose feature suitable for administration into the oral cavity for inhalation, or into the nasal passageways, thereby delivering a precise amount of aerosol per use.

Powders may be formed with the aid of any suitable powder base, e.g., talc, lactose, starch, etc. Drops may be formulated with an aqueous base or nonaqueous base also comprising one or more dispersing agents, suspending agents, solubilizing agents, etc.

Also included are solid form preparations which are intended to be converted, shortly before use, to liquid form preparations for therapeutic administration, such as solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation with a syringe, teaspoon or other volumetric container. When multiple liquid doses are so prepared, it is preferred to maintain the unused portion of said liquid doses at low temperature (i.e., under refrigeration) in order to retard possible spoilage or decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses each of which contain an appropriate quantity of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from about 0.1 mg to about 1000 mg. according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration will be regulated according to the judgment of the attending clinician based upon such factors as age, condition and size of the patient, severity of the disease being treated and the particular compound which is used.

The following formulations exemplify some of the dosage forms of the compositions of this invention. In each, the term "active compound" designates the compound 5-(4-piperidinylmethyl)aminosulfonyl isoquinoline. However, any other compound represented by formula I could be substituted therefore. Consequently, the scope of the invention is not to be limited thereby.

Pharmaceutical Dosage Form Examples

Example A

| No. | Ingredient | Tablets mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|   | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼″) if needed. Dry the damp granules. Screen the dried granules if needed and mix with Item No. 4 and mix for 10–15 minutes. Add item No. 5 and mix for 1–3 minutes. Compress the mixture to appropriate size and weight on a suitable table machine.

| No. | Ingredient | Capsules mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|   | Total | 250 | 700 |

Method of Manufacture

Mix Item Nos. 1, 2 and 3 in a suitable blender 10–15 minutes. Add Item No. 4 and mix for 1-3 minutes. Fill the mixture into suitable two-piece hard gelatin capsules on a suitable encapsulating machine.

Example C

| Ingredient | Parenteral mg/vial | mg/vial |
|---|---|---|
| Active Compound Sterile Powder | 100 | 500 |

Add sterile water for injection or bacteriostatic water for injection, for reconstitution.

Example D

| Ingredient | Injectable mg/vial |
|---|---|
| Active Compound | 100 |
| Methyl p-hydroxybenzoate | 1.8 |
| Propyl p-hydroxybenzoate | 0.2 |
| Sodium Bisulfite | 3.2 |
| Disodium Edetate | 0.1 |
| Sodium Sulfate | 2.6 |
| Water for Injection q.s. ad | 1.0 ml |

Method of Manufacture (for 1000 vials)

1. Dissolve p-hydroxybenzoate compounds in a portion (85% of the final volume) of the water for injection at 65°–70° C.
2. Cool to 25°–35° C. Charge and dissolve the sodium bisulfite, disodium edetate and sodium sulfate.
3. Charge and dissolve active compound.
4. Bring the solution to final volume by added water for injection.
5. Filter the solution through 0.22 membrane and fill into appropriate containers.
6. Finally sterilize the units by autoclaving.

Example E

| Nasal Spray | mg/ml |
|---|---|
| Active Compound | 10.0 |
| Phenyl Mercuric Acetate | 0.02 |
| Aminoacetic Acid USP | 3.7 |
| Sorbitol Solution, USP | 57.0 |
| Benzalkonium Chloride Solution | 0.2 |
| Sodium Hydroxide 1N Solution to adjust pH | — |
| Water Purified USP to make | 1.0 ml |

Example F

| Inhalation Aerosol | |
|---|---|
| Active ingredient (solution) | 17.2 g |
| Propellant e.g., compressed $CO_2$ gas | 5 to 10% |

Package active ingredient under 15–20 psig in a seamless aluminum container (15–45 ml), which may be coated on its interior with any suitable coating agent. Cap the container with an appropriate activator, such as a mechanical breakup activator. A metered dose feature should also be included to enable the administration of a precise amount of active ingredient per inhalation, such as from about 0.01 mg to about 10 mg per puff.

Also, one or more preservatives, antioxidants, solvents or other pharmacologically inactive, pharmaceutically acceptable ingredients may be added as appropriate.

The following chemical reactions and examples are intended to illustrate preparation of the compounds of the invention, but not intended to limit the present invention.

PREPARATIVE EXAMPLE I

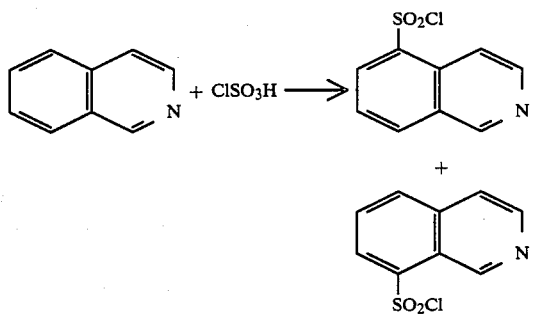

5- and 8-Chlorosulfonyl Isoquinolines

Charge a 1 liter, 3 necked round bottom flask equipped with a reflux condensor, drying tube, 250 ml non-pressure equalizing addition funnel, and a mechanical stirrer with 450 g of chlorosulfonic acid (3.86 moles 4.5 equiv.) and cool in an ice bath. When cold, add isoquinoline (100 ml, 0.85 moles, 1 equiv.) at a rate sufficient to keep the strongly exothermic reaction under control. The solution becomes dark and a large amount of solid is formed. Total addition time is about 30 minutes. When addition is complete replace the ice bath with a heating mantle and heat the mixture to reflux for two hours. Reflux is accompanied by the evolution of gas.

Cool the mixture to room temperature. Pour the viscous mixture slowly onto 5 liters of ice in a large mechanically stirred extractor in a well ventilated hood. Rinse the flask residue with dichloromethane, and add dichloromethane to bring the total organic volume to 3 liters. With the extractor running, add solid sodium carbonate until the pH of the aqueous later exceeds 9.0.

Separate the dark yellow organic layer and the water layer and extract with an additional liter of dichloromethane. Combine the organic extracts, dry over magnesium sulfate, filter and concentrate on a rotary evaporator. Remove the solvent by overnight pumping on a high vacuum line to yield an orange residue. Separate the residue into the 5- and 8-isoquinoline sulfonyl chloride fractions using silica gel chromatography.

PREPARATIVE EXAMPLE II

5- and 8-Quinoline Sulfonyl Chlorides

Substitute quinoline in the reaction described in Preparative Example I to prepare the 5- and 8-quinoline sulfonyl chloride compounds.

EXAMPLE I 5-(4-piperidinylmethylaminosulfonyl) isoquinoline

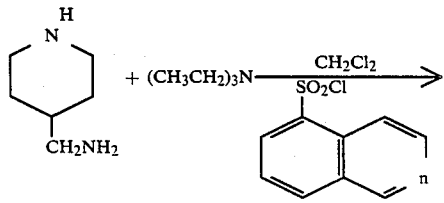

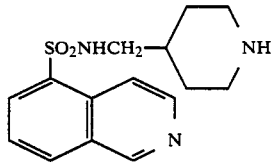

Dissolve 5.02 g of 4-aminomethylpiperidine and 22 g of triethylamine in 50 ml of dichloromethane. Add dropwise over 30 minutes 5.0 g of 5-isoquinoline sulfonyl chloride dissolved in 50 ml of dichloromethane while cooling the mixture in an ice bath. Stir at room temperature for 72 hours. Filter the reaction mixture and evaporate the filtrate. Chromatograph the residue over 400g of silica gel eluting with dichloromethane/methanol (9/1). Obtain the title compound by evaporating the appropriate fractions, as determined by thin layer chromatography. Dissolve the product in ethanol saturated with HCl and evaporate to obtain the title compound as the dihydrochloride salt. FAB MS $(M+1)_e = 306$.

EXAMPLE II

Substitute the precursor compound A-NH$_2$ from Col. 1 of Table A below into the reaction process of Example I to make a compound of the invention appearing in column 2 below.

TABLE A

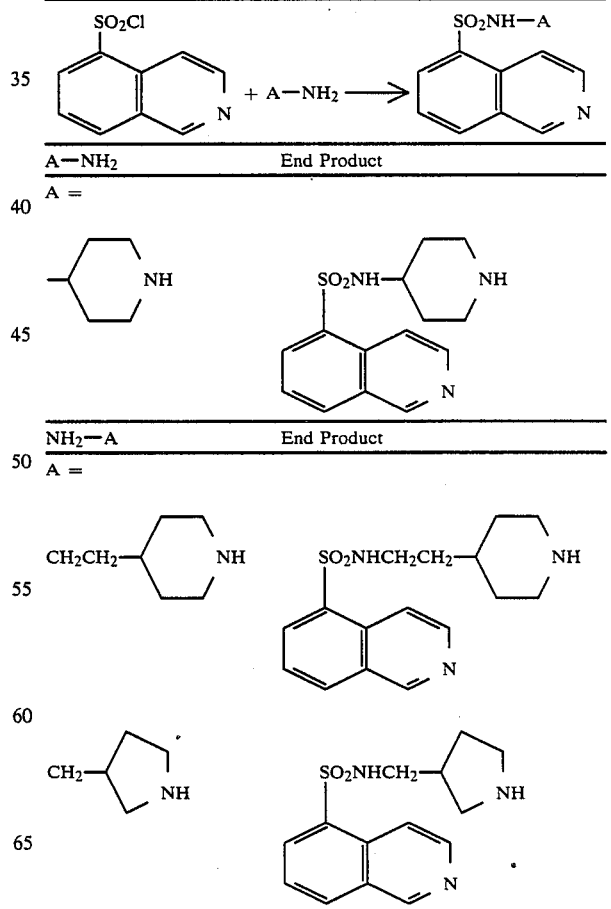

TABLE A-continued

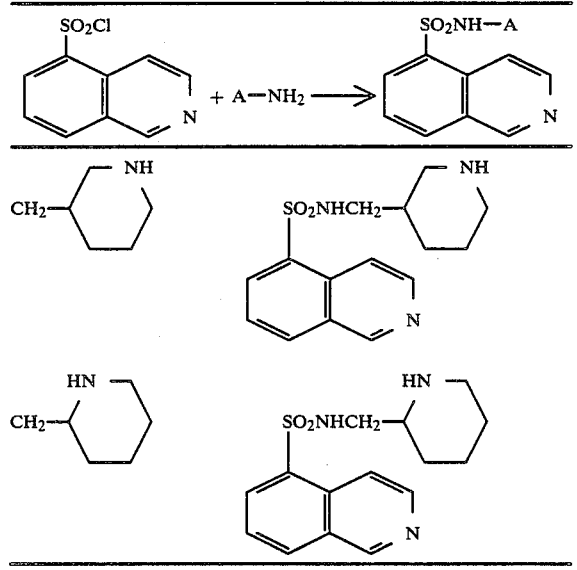

EXAMPLE III 5-(1-tert-butyloxycarbonyl-4-piperidinylaminomethyl-sulfonyl) isoquinoline

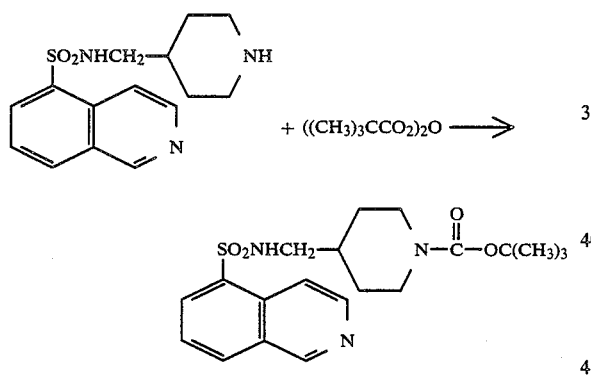

Dissolve 3.05 g of the title compound of Example I in 20 ml of DMF. Add 2.138 g of di-tert-butyl dicarbonate while stirring, and cooling in an ice bath. Stir 12 hours at room temperature and evaporate the solvent under high vacuum. Dissolve the residue in dichloromethane and wash with water. Dry the organic layer with anhydrous magnesium sulfate and evaporate the solvent to obtain the title compound.

EXAMPLE IV 5-(4-piperidinylmethyl(N-methyl)aminosulfonyl) isoquinoline

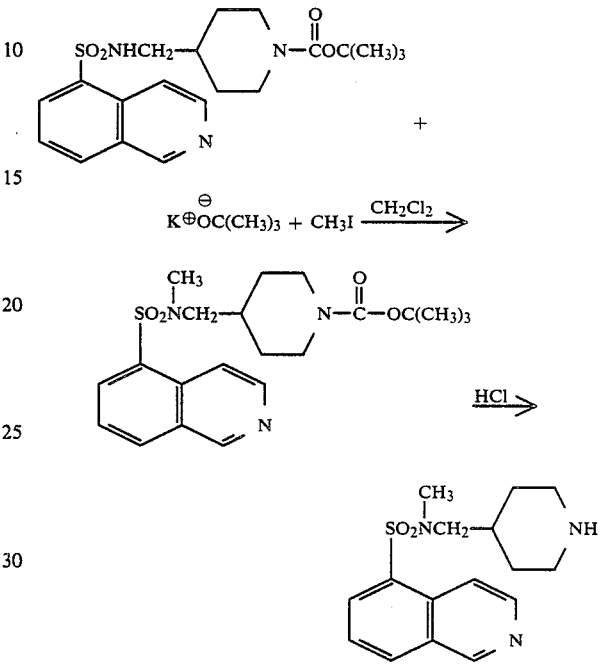

Dissolve 4.05 g of the title compound of Example III in 20 ml of DMF. Cool the reaction to 0° C. in an ice-bath and add 1.12 g of potassium tert-butoxide and stir for 10 minutes. Add 1.42g of methyl iodide and stir for 1 hr. at 0° C., and for 1 hour at room temperature. Evaporate the solvent under high vacuum. Dissolve the residue in dichloromethane and wash with water. Dry the organic layer with anhydrous magnesium sulfate and evaporate the solvent to obtain the title compound.

Add 30 ml of 6 M HCl dissolved in dioxane to the title compound, and stir for 1 hour at room temperature. Evaporate the solvent to obtain the title compound as its dihydrochloride salt.

EXAMPLE V 5-(1-methyl-4-piperidinylmethylaminosulfonyl) isoquinoline

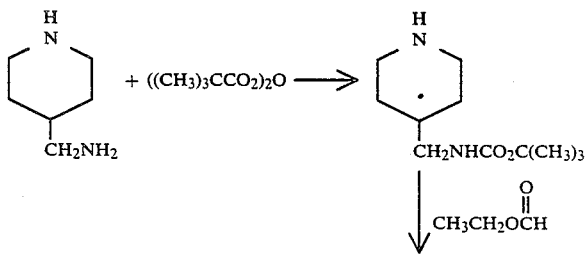

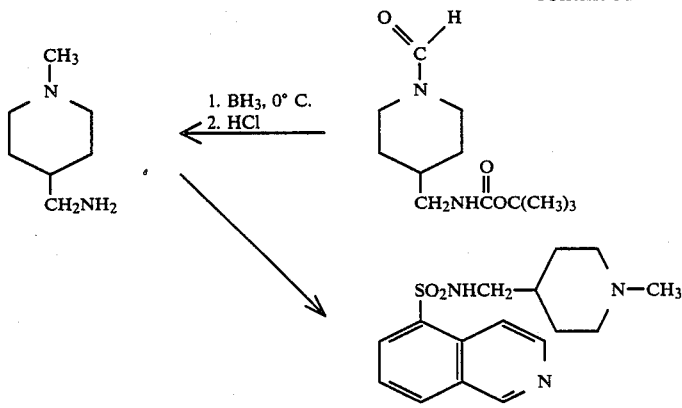

A. Dissolve 1.14 g of 4-aminomethylpiperidine and 2.18 g of di-tert-butyl dicarbonate in 10 ml of dichloromethane. Stir 12 hours at room temperature. Dilute the mixture with 40 ml of dichloromethane and wash with saturated NaCl solution. Dry the organic layer with anhydrous magnesium sulfate and evaporate the solvent to obtain the product, 4-tert butyloxycarbonylaminomethyl piperidine.

B. Dissolve the product of part A above in 20 ml of ethyl formate and reflux for 12 hours. Evaporate the solvent to dryness to obtain the product 1-formyl-4-tert-butyloxycarbonylaminomethyl piperidine.

C. Dissolve the product of part B above in 10 ml of anhydrous tetrahydrofuran (THF), cool to 0° C. and add dropwise to 10 ml of 1 M borane dissolved in THF at 0° C. Stir for 8 hours at 0° C. and add 5 ml of 12N HCl. Reflux for 1 hour. Evaporate the solvent to a dry residue and add 50 ml of methanol. Evaporate to obtain the product 1-methyl-4-aminomethylpiperidine, as the dihydrochloride salt.

Substitute the product of part C above in the reaction scheme described in Example I to obtain the title compound.

EXAMPLE VI 5-(1,1-dimethyl-4-piperidinylmethylaminoulfonyl) isoquinoline

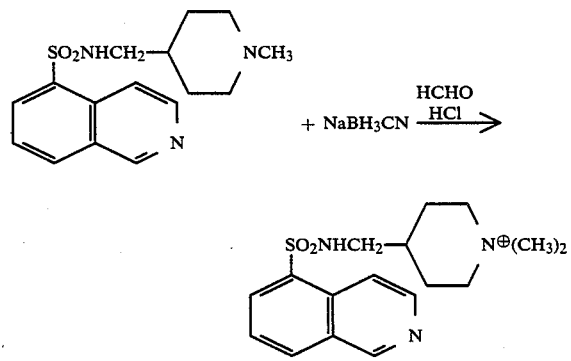

Dissolve the title compound of Example V above in 10 ml of 40% aqueous formaldehyde. Add 1.16 g of NaBH₃CN and stir for 4 hours at room temperature. Add 2 ml of 12 N HCl and stir for 1 hour at room temperature. Evaporate the solvent to obtain the title compound as its chloride, hydrochloride salt.

EXAMPLE VII 5-(I-aminoiminomethyl-4-piperidinylmethylaminosulfonyl) isoquinoline

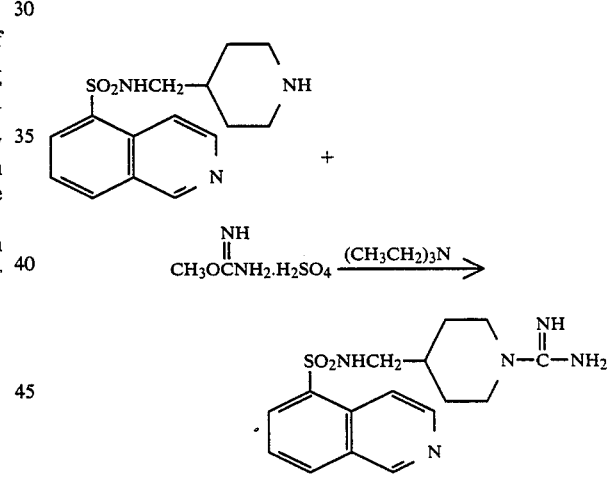

Dissolve the title compound of Example I in 50 ml of DMF. Add 4.44 g of triethylamine and 3.78 g of O-methyl-isourea hydrogen sulfate and heat at 50° C. for 2 hours. Cool the reaction and evaporate the solvent. Dissolve the residue in water and pass through a column of Dowex-1 (Cl⁻ form) resin eluting with water. Lyophilize the eluate to obtain the title compound as the dihydrochloride salt.

While Applicants have provided numerous chemical reactions and forms of the compounds of the invention, numerous other species of compounds falling within the scope of the claims are contemplated as being a part of the invention, as defined by the claims. Consequently the scope of this invention includes all such compounds, and the scope of the invention is not limited to the specific teachings herein.

We claim:

1. A compound represented by the structural formula I

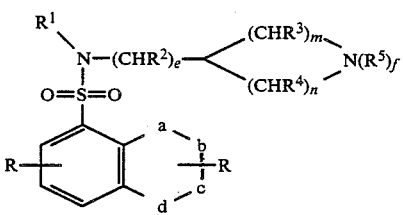

or a pharmaceutically acceptable salt or solvate thereof wherein:
one of a, b, c and d is =N— and the remaining a, b, c and d groups are =CH— one of which may be substituted with R;
R optionally represents halo, hydroxy, lower alkyl, alkenyl, alkynyl, or aryl;
$R^1$ and $R^2$ independently represent H or lower alkyl;
e is an integer of from 0 to 5;
$R^3$ and $R^4$ independently represent H, lower alkyl, alkenyl, alkynyl, or aryl;
m and n are independently 0, 1, 2, 3 or 4 such that the sum of m and n is 3, 4, 5 or 6; and
$R^5$ represents H, lower alkyl, aminoiminomethyl, —$CO_2R^a$ or lower alkyl substituted with —$CO_2R^a$, where $R^a$ is H or lower alkyl, such that when $R^5$ is H or lower alkyl, f is an integer 1 or 2, and when $R^5$ is —$CO_2R^a$ or aminoiminomethyl, f is 1.

2. A compound as defined in claim 1 wherein c is =N— and a, b and d are =CH—.

3. A compound as defined in claim 1 where b is =N— and a, c and d are =CH—.

4. A compound as defined in claim 1 where a is =N— and b, c and d are =CH—.

5. A compound as defined in claim 1 where d is =N— and a, b and c are =CH—.

6. A compound as defined in claim 1 wherein $R^1$ is H.

7. A compound as defined in claim 1 where $R^1$ is lower alkyl.

8. A compound as defined in claim 7 where $R^1$ is methyl.

9. A compound as defined in claim 1 where $R^2$ is H and e is 0, 1 or 2.

10. A compound as defined in claim 9 where e is 0 or 1.

11. A compound as defined in claim 1 wherein m is 2 and n is 2.

12. A compound as defined in claim 1 where m is 1 and n is 2 or 3.

13. A compound as defined in claim 1 where $R^5$ represents H or lower alkyl.

14. A compound as defined in claim 13 where $R^5$ represents methyl or ethyl.

15. A compound or pharmaceutically acceptable salt or solvate thereof which is:
5-(4-piperidinylmethylaminosulfonyl) isoquinoline;
5-(4-piperidinylaminosulfonyl) isoquinoline;
5-(4-piperidinylethylaminosulfonyl) isoquinoline;
5-(3-pyrrolidinylmethylaminosulfonyl) isoquinoline;
5-(3-piperidinylmethylaminosulfonyl) isoquinoline;
5-(2-piperidinylmethylaminosulfonyl) isoquinoline;
5-(1-tert-butyloxycarbonyl-4-piperidinylaminosulfonyl) isoquinoline;
5-(4-piperidinylmethyl(N-methyl)aminosulfonyl) isoquinoline;
5-(1-methyl-4-piperidinylmethylaminosulfonyl) isoquinoline;
5-(1,1-dimethyl-4-piperidinylmethylaminosulfonyl) isoquinoline, or
5-(1-aminoiminomethyl-4-piperidinylmethylaminosulfonyl) isoquinoline.

16. 5-(4-piperidinylmethylaminosulfonyl) isoquinoline.

17. A pharmaceutical composition comprising a compound as defined in claim 1 in combination with a pharmaceutically acceptable carrier.

18. The pharmaceutical composition of claim 17 in the form of a tablet.

19. The pharmaceutical composition of claim 17 in the form of a capsule.

20. The pharmaceutical composition of claim 17 in the form of a nasal spray.

21. The pharmaceutical composition of claim 17 in the form of an inhalation aerosol.

22. A method of treating allergy in a mammal comprising administering to said mammal in need of such treatment an anti-allergic effective amount of a compound as defined in claim 1.

* * * * *